United States Patent
Miesak

(10) Patent No.: US 9,804,096 B1
(45) Date of Patent: Oct. 31, 2017

(54) SYSTEM AND METHOD FOR DETECTING LATENT IMAGES ON A THERMAL DYE PRINTER FILM

(71) Applicant: Leidos Innovations Technology, Inc., Gaithersburg, MD (US)

(72) Inventor: Edward Miesak, Windermere, FL (US)

(73) Assignee: Leidos Innovations Technology, Inc., Gaithersburg, MD (US)

( * ) Notice: Subject to any disclaimer, the term of this patent is extended or adjusted under 35 U.S.C. 154(b) by 473 days.

(21) Appl. No.: 14/596,608

(22) Filed: Jan. 14, 2015

(51) Int. Cl.
| | |
|---|---|
| H04N 1/00 | (2006.01) |
| G01N 21/84 | (2006.01) |
| H04N 1/06 | (2006.01) |
| G07D 7/121 | (2016.01) |
| G06K 9/00 | (2006.01) |

(52) U.S. Cl.
CPC ......... *G01N 21/84* (2013.01); *G06K 9/00013* (2013.01); *G07D 7/121* (2013.01); *H04N 1/00843* (2013.01); *H04N 1/06* (2013.01)

(58) Field of Classification Search
CPC .............. G01N 21/84; G06K 9/00013; H04N 1/00843; H04N 1/06
USPC ......................................................... 348/110
See application file for complete search history.

(56) References Cited

U.S. PATENT DOCUMENTS

| | | | |
|---|---|---|---|
| 4,120,585 A | 10/1978 | DePalma et al. | |
| 4,247,784 A | 1/1981 | Henry | |
| 4,351,588 A | 9/1982 | Zullig | |
| 4,632,807 A | 12/1986 | Marsoner | |
| 4,783,167 A | 11/1988 | Schiller et al. | |
| 4,785,171 A | 11/1988 | Dowling, Jr. et al. | |
| 4,794,260 A | 12/1988 | Asano et al. | |
| 4,989,968 A | 2/1991 | Freedman | |
| 5,004,349 A | 4/1991 | Sato et al. | |
| 5,099,131 A | 3/1992 | Brownrigg et al. | |
| 5,109,427 A | 4/1992 | Yang | |
| 5,123,723 A | 6/1992 | Chesnutt et al. | |
| 5,210,588 A | 5/1993 | Lee | |
| 5,233,404 A | 8/1993 | Lougheed et al. | |

(Continued)

FOREIGN PATENT DOCUMENTS

| | | |
|---|---|---|
| CN | 2603449 | 2/2004 |
| CN | 201210214 | 3/2009 |

(Continued)

OTHER PUBLICATIONS

James Robertson, 2004 by CRC Press LLC, "The Practice of Crime Scene Investigation" (pp. 1-424).

(Continued)

*Primary Examiner* — Jeffery Williams
(74) *Attorney, Agent, or Firm* — Oblon, McClelland, Maier & Neustadt, L.L.P.

(57) ABSTRACT

A system is disclosed including a cylindrical device, having at least one transparent path therethrough, configured to support a thermal dye printer film, the film comprising at least one color panel, a light source configured to illuminate through the cylindrical device at an absorption wavelength of the at least one color panel of the film, and an imaging device configured to capture an image of the film with light emitted at the absorption wavelength of the at least one color panel of the film at a target location on the cylindrical device. Another system and a method are also disclosed.

22 Claims, 6 Drawing Sheets

(56) References Cited

U.S. PATENT DOCUMENTS

| | | | |
|---|---|---|---|
| 5,266,805 A | 11/1993 | Edgar | |
| 5,313,265 A | 5/1994 | Hayes et al. | |
| 5,629,764 A | 5/1997 | Bahuguna et al. | |
| 5,720,772 A | 2/1998 | Eckhouse | |
| 5,812,252 A | 9/1998 | Bowker et al. | |
| 5,912,768 A | 6/1999 | Sissom et al. | |
| 5,963,657 A | 10/1999 | Bowker et al. | |
| 6,005,963 A | 12/1999 | Bolle et al. | |
| 6,115,484 A | 9/2000 | Bowker et al. | |
| 6,124,238 A | 9/2000 | Chapman et al. | |
| 6,127,189 A | 10/2000 | Joullie et al. | |
| 6,144,453 A | 11/2000 | Hallerman et al. | |
| 6,193,425 B1 | 2/2001 | Edgar | |
| 6,292,576 B1 | 9/2001 | Brownlee | |
| 6,354,724 B1 | 3/2002 | Sakashita | |
| 6,485,981 B1 | 11/2002 | Fernandez | |
| 6,488,892 B1 | 12/2002 | Burton et al. | |
| 6,503,695 B1 | 1/2003 | Miyazawa et al. | |
| 6,558,052 B2 | 5/2003 | Edgar | |
| 6,643,390 B1 | 11/2003 | Clark et al. | |
| 6,665,427 B1 | 12/2003 | Keagy et al. | |
| 6,668,071 B1 | 12/2003 | Minkin et al. | |
| 6,885,017 B2 | 4/2005 | Lee et al. | |
| 6,989,547 B2 | 1/2006 | Lee et al. | |
| 6,995,384 B2 | 2/2006 | Lee et al. | |
| 7,039,224 B2 | 5/2006 | Hamid et al. | |
| 7,181,052 B2 | 2/2007 | Fujieda | |
| 7,212,330 B2 | 5/2007 | Seo et al. | |
| 7,234,641 B2 | 6/2007 | Olmstead | |
| 7,295,688 B2 | 11/2007 | Hara et al. | |
| 7,310,153 B2 | 12/2007 | Kiesel et al. | |
| 7,346,200 B1 | 3/2008 | Tsipouras et al. | |
| 7,408,641 B1 | 8/2008 | Kwak et al. | |
| 7,420,663 B2 | 9/2008 | Wang et al. | |
| 7,489,391 B2 | 2/2009 | Engheta et al. | |
| 7,787,110 B2 | 8/2010 | Raguin et al. | |
| 7,846,191 B2 | 12/2010 | Vaynberg et al. | |
| 8,077,929 B2 | 12/2011 | Heidt | |
| 8,180,120 B2 | 5/2012 | Hook | |
| 8,371,695 B2 | 2/2013 | Papac et al. | |
| 8,396,319 B2 | 3/2013 | Pugh, Jr. et al. | |
| 8,437,517 B2 | 5/2013 | Miesak et al. | |
| 8,805,033 B2 | 8/2014 | Miesak et al. | |
| 9,188,546 B2 | 11/2015 | Miesak et al. | |
| 2002/0190212 A1 | 12/2002 | Boas et al. | |
| 2003/0118219 A1 | 6/2003 | Higuchi et al. | |
| 2003/0156284 A1 | 8/2003 | Farr | |
| 2003/0156740 A1 | 8/2003 | Siegel et al. | |
| 2003/0185425 A1 | 10/2003 | Nishikawa | |
| 2004/0026635 A1 | 2/2004 | Lee et al. | |
| 2005/0141756 A1 | 6/2005 | Lee et al. | |
| 2006/0008129 A1 | 1/2006 | Lee et al. | |
| 2006/0120573 A1 | 6/2006 | Iori | |
| 2006/0126168 A1 | 6/2006 | Treado et al. | |
| 2007/0177233 A1 | 8/2007 | Ichikawa et al. | |
| 2007/0201733 A1 | 8/2007 | Hara | |
| 2008/0198379 A1 | 8/2008 | Coker et al. | |
| 2008/0204710 A1 | 8/2008 | Harrison et al. | |
| 2009/0052752 A1 | 2/2009 | Monden | |
| 2009/0127475 A1 | 5/2009 | De Lamberterie | |
| 2009/0155456 A1 | 6/2009 | Benkley et al. | |
| 2010/0303311 A1 | 12/2010 | Shin et al. | |
| 2010/0311005 A1 | 12/2010 | Liang | |
| 2011/0076383 A1 | 3/2011 | Reedy et al. | |
| 2011/0121758 A1 | 5/2011 | Bierhuizen et al. | |
| 2012/0105586 A1 | 5/2012 | Miesak et al. | |
| 2012/0138728 A1 | 6/2012 | Brunton et al. | |
| 2013/0301887 A1 | 11/2013 | Miesak et al. | |
| 2014/0254894 A1 | 9/2014 | Miesak et al. | |
| 2015/0317505 A1* | 11/2015 | Miesak | G06K 9/00013 382/124 |
| 2015/0338745 A1 | 11/2015 | Fukazawa | |
| 2016/0026845 A1 | 1/2016 | Miesak et al. | |

FOREIGN PATENT DOCUMENTS

| | | |
|---|---|---|
| JP | 05-220131 | 8/1993 |
| JP | 06-147852 | 5/1994 |
| JP | 2001034738 | 2/2001 |
| WO | 2006073450 | 7/2006 |
| WO | 2010064034 | 6/2010 |
| WO | 2010071215 | 6/2010 |

OTHER PUBLICATIONS

Bartick et al., 2002, "Spectrochemical Analysis and Hyperspectral Imaging of latent Fingerprints" (pp. 61-64).

Austin Richards, Mar. 28, 2010, "Reflected Ultraviolet Imaging for Forensics Applications" (pp. 1-31).

Tahtouh et al., 2005, "The Detection and Enhancement of Latent Fingermaks Using Infrared Chemical Imaging" (pp. 1-9).

"Forensic Lab 8.0: Revealing Latent Fingerprints—Introduction", Aug. 16, 2009, pp. 1-17.

Seto, Eileen K. et al. "Imaging Electrophoretic Gels with a Scanning Beam Laser Macroscope," Electrophoresis, Wiley Interscience, DE, Apr. 15, 2005, pp. 934-940, vol. 16.

"Chapter 2: Finger Mark Examination Techniques within Scope of ISO 17025 2.1 Visual Examination," Mar. 26, 2013, pp. 291-293, XP055130668.

Heisel, Francine, Laser-Induced Fluorescence Imaging for Monitoring Nitrogen Fertilizing Treatments of Wheat, Proceedings of SPIE, Issue 1, pp. 10-21, Jul. 2, 1997.

* cited by examiner

SYSTEM AND METHOD FOR DETECTING LATENT IMAGES ON A THERMAL DYE PRINTER FILM

BACKGROUND

Embodiments relate to detecting latent images and, more particularly, to detecting latent images left on a thermal dye printer film.

A thermal dye printer, dye-sublimation printer or dye-sub printer is a computer printer which employs a printing process that uses heat to transfer dye onto materials such as a plastic, card, paper, or fabric. Many consumer and professional dye-sublimation printers are designed and used for producing such items as, but not limited to, photographic prints, identification ("ID") cards, etc.

The thermal dye printer produces continuous-tone images that look very much like photographic film. Thermal dye printers include a print cartridge that contains a cellophane covered thermal dye printer film having a plurality of stored panels of dye having the same dimensions as the page printed. There are generally four different panels for each print, one color panel each of cyan, magenta and yellow (CMY) and a final clear (K) coat panel or overcoat (O) panel that allows the printed image on special dye-receptive paper to be handled immediately without smudging.

Heat releases the CMY dyes from the film. The paper and film are passed together under the print head for each color panel, so that the process lays one color at a time from the film. The print head may contain thousands of heating elements that produce varying amounts of heat. The hotter the element, the more dye is released. By varying the temperature, selectable shades of each color can be overlaid on top of each other. The dyes blend into continuous-tone color image in the paper. The imaged paper is then sealed by the protective final clear overcoat (K) layer to provide water-resistant and UV blocking barrier that also prevents smudging, helping to ensure the preservation of images.

Counterfeiters can use a variety of different printers to print counterfeit bills/currency. Laser printers and inkjet printers have been used for this purpose. A problem with laser printers and inkjet printers for counterfeiting is that they cannot replicate the government-issue hidden strips. It is known that thermal dye printers using a first and second printing process can print bills that include the government-issue strips.

Once the film for a thermal dye printer is used, a latent image of what was printed is usually left on the film. In order to capture and successfully prosecute counterfeiters, a method and system to obtain latent images left on a thermal dye printer film is desired. However, such film is usually crinkled and crushed which makes acquiring images from the film that much more difficult. Furthermore, if handled improperly, the film is likely to tear or rip. Thus, there is a need for any such method and system to be able to acquire a latent image from such film that may be crinkled, crushed, torn, or fragile enough to tear.

SUMMARY

Embodiments relate to a system and a method for capturing latent images from a dye printer film. The system comprises a cylindrical device, having at least one transparent path therethrough, configured to support a thermal dye printer film, the film comprising at least one color panel. The system also comprises a light source configured to illuminate through the cylindrical device at an absorption wavelength of the at least one color panel of the film. The system also comprises an imaging device configured to capture an image of the film with light emitted at the absorption wavelength of the at least one color panel of the film at a target location on the cylindrical device.

A system for capturing a latent image from a thermal dye printer film having a plurality of color panels is also disclosed. The system comprises an arcuate surface configured to provide for removal of a deformation in a thermal dye printer film and with a transparent path through the arcuate surface. The system also comprises a light source configured to illuminate through the arcuate surface at an absorption wavelength of at least one of the color panels of the film. The system also comprises an imaging device configured to capture an image of the film with light emitted at the absorption wavelength of the at least one color panel of the film at a target location on the arcuate surface.

The method comprises removing deformation of a thermal dye printer film having a plurality of color panels with a cylindrical device configured to support the thermal dye printer film, illuminating a light through a target section on the roller at an absorption wavelength of at least one of the color panels of the film, and capturing an image of the light emitted at the absorption wavelength of the at least one of the color panels of the film through the cylindrical device at the target section on a surface of the cylindrical device.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
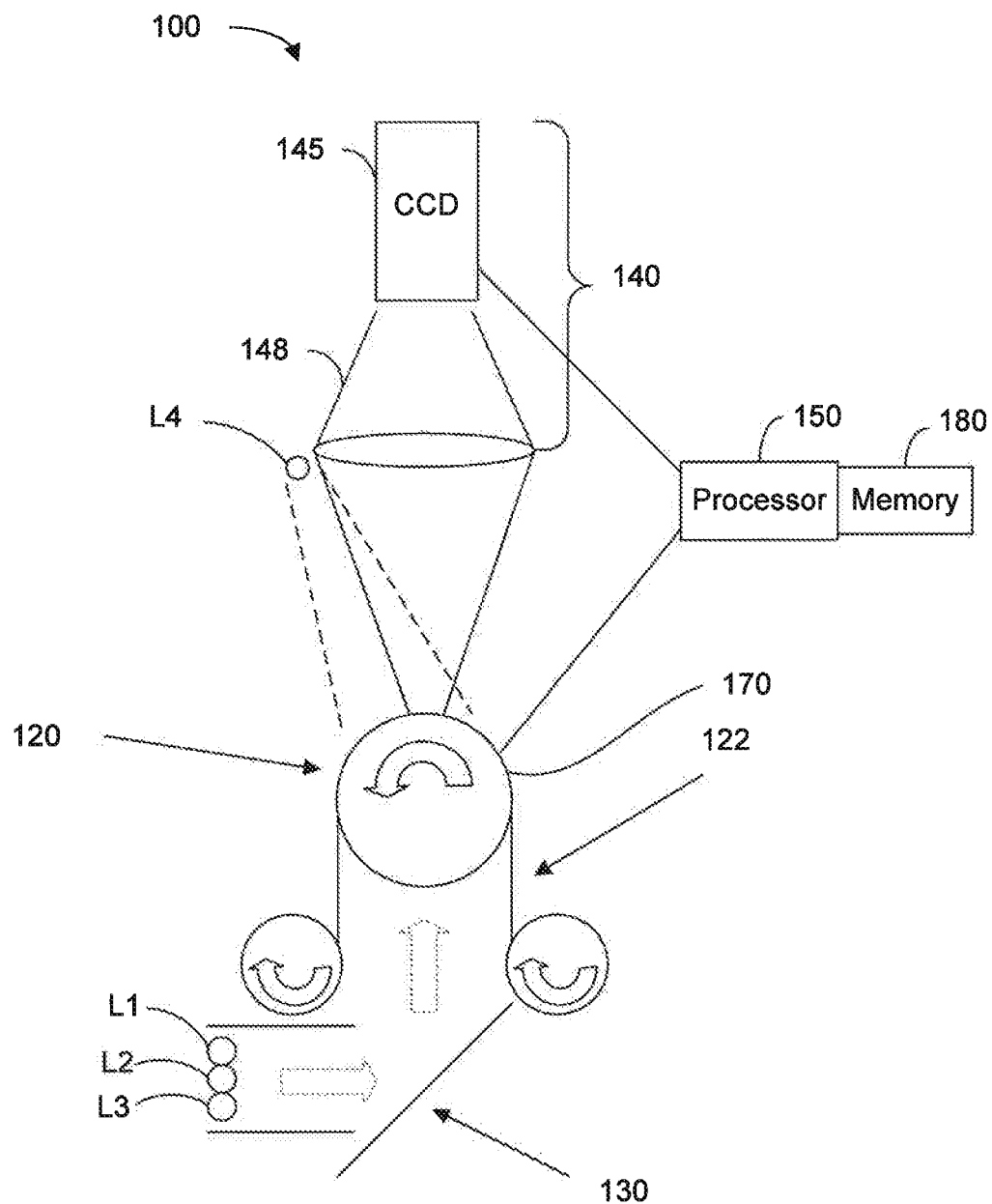
FIG. 1 illustrates an embodiment of a system.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

As used herein the term "latent image" may refer to an image left on a used thermal dye printer film. This term may also include a latent fingerprint left on the film. Therefore this term is not meant to be limiting. As explained in detail below, the system and method disclosed herein may be used so that an original image can be reconstructed and/or personal handling the film may be identified based on markings left on the film.

FIG. 1 is a block diagram of an embodiment of a system. The system 100 may be used for imaging used thermal dye printer film. Images may be obtained from smooth/glossy film as well as matte (having a dull or lusterless surface) film surfaces regardless of the condition of the film. Wavelength dependent image contrast as described herein aids in obtainable image quality from the used film. The system 100 may include a roller 120, cylindrical device or arcuate surface, which may be transparent. The roller 120 may support the film 122 while allowing illuminated light to propagate through the film 122. More specifically, the roller 120 may provide for a surface where a target section on the roller is provided to smooth or remove creases, wrinkles or crinkles from the film at the target section. This may be accomplished simply by laying the film over the cylindrical device and allowing gravity to smooth out the film, at least at a center line location where the film contacts the cylindrical device. Thus, the target section or target area may be limited to a line extended across a segment of the cylindrical device. Thus, the transparent roller 120 may be oriented to use gravity to help smooth out wrinkles in the film 122.

The cylindrical device may be transparent, or at least one transparent path may be provided therethrough the cylindrical device. By being transparent, the roller 120 may further act as an optical lens concentrating the illuminating light along its length where it is needed. The transparency may be provided in a wavelength range of interest. As a non-limiting example, the wavelength may be generally at least throughout the range from 400 nanometer ("nm") to 700 nm. Using the transparent roller 120 may assist in providing for a compact system when compared with a non-transparent roller used in the system 100.

The imaging system 100 may include several light sources L1, L2 and L3 which provide first, second, third narrow band light source for illuminating the first, second and third color panel, or the cyan, magenta and yellow (CMY) panels at or near a maximum absorption wavelength for the respective color panels. Each panel of the film may be scanned with a specific wavelength narrow band light, represented by L1, L2 and L3, to generally provide for optimum contrast of each panel. Thus, the light sources, L1, L2, and L3 operate as a back light that illuminates through the roller 120. A uniform diffuse reflector 130 may be provided to increase uniformity of the lighting. The diffuse reflector 130 may be provided as opposed to a diffuser in which light passes through because the diffuse reflector 130 may provide for more uniform light distribution. Another light source L4 may be provided in the system 100 and illuminated at a critical angle to reveal any latent fingerprints that may be present on the film 120 which may be imaged using the same imaging device and lens system.

An imaging device 140, such as, but not limited to, a camera 145 and a lens 148 may used to collect the latent images. In one non-limiting embodiment the camera 145 may be a digital B/W CCD camera. The imaging device 140 may be configured to take images of the film, line by line. More specifically, the imaging device 140 may take an image of a target area 170 on the roller 120 where the film is positioned. Once the image is taken, the film 120 may be moved so that an adjacent position of the film is then placed at the target area for taking another image. A processor 150 may then be provided to combine each image taken into a combined final image.

Figure 2:
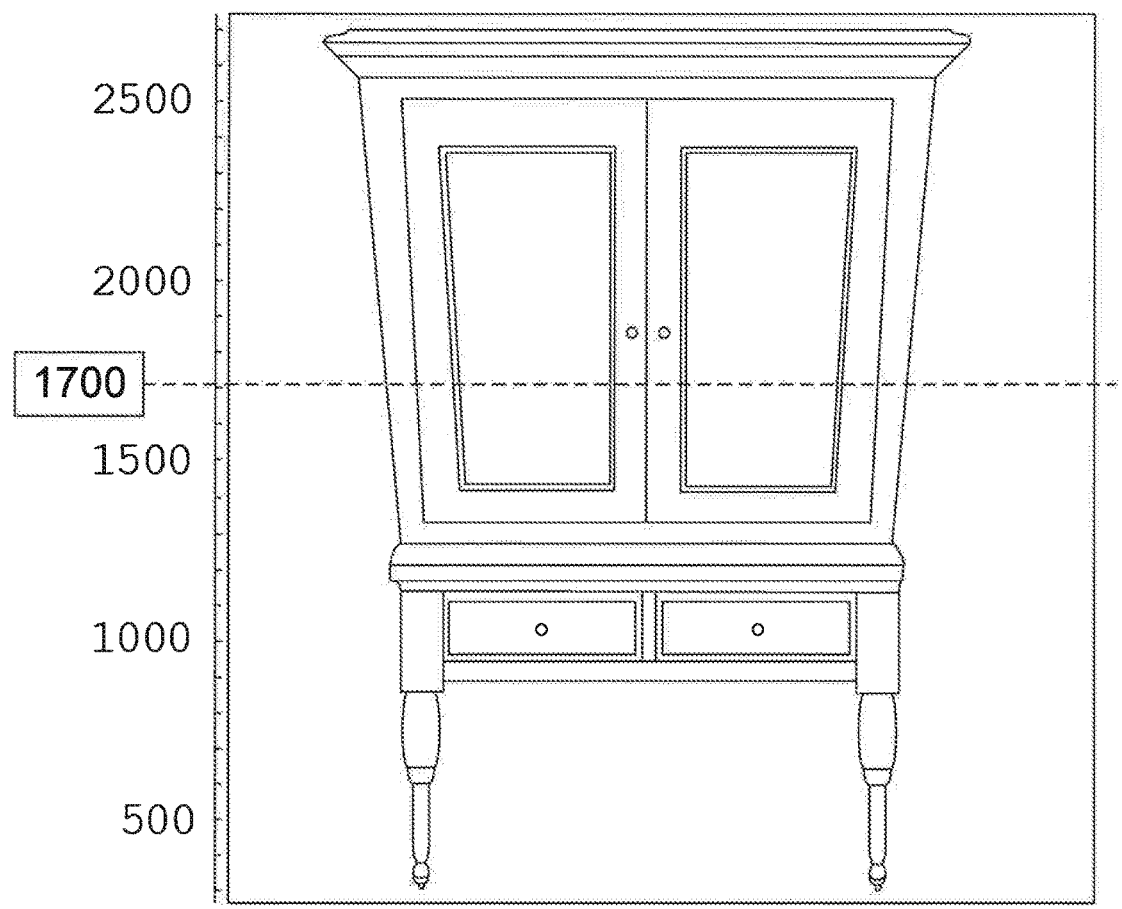
FIG. 2 illustrates an embodiment of an image on a film.

Thus, in operation, the film 122 does not have to be stretched out to be imaged. Instead, as illustrated in FIG. 2, one line of image may be obtained along the length of the roller 120, and the complete image can be constructed line by line, such as with the processor 150. The image in FIG. 2 is shown with respective lines of the image numbered where line 1700 is the line currently being imaged.

The film 122 may be stretched on the transparent roller 120 along the line where it is imaged. This eases any problem of negative results of stretching the film 122 flat because it only has to be flat along a thin (illumination) region or target section.

The film 122 and transparent roller 120 may be stepped together through each frame one line of pixels at a time. The imaging device 140 and illumination from the light sources, L1, L2, L3, L4 may operate on the entire width of each frame simultaneously or in another embodiment, sequentially. The stepping process may be controlled by the processor 150 which may generally also control the illumination level of the light sources and the imaging device 140. Thus, the system 100 may effectively scan the used C, Y, M and clear (K) panels of the film to recover the previously printed images as well as any latent fingerprints that may be present.

In another non-limiting embodiment, the imaging device 140 may collect latent images using a $\gamma$ (gamma) setting of $\cong 1.0$ and latent fingerprint images at a critical angle using a setting of $\gamma \cong 0.1$ (gamma compression). The gamma values may be adjusted depending on the image content. The image data information generated by the camera 145 may be coupled to a processor 150 that may include memory 180 having stored algorithms that reconstruct the original image as well as fingerprints (if present) from the image data provided by camera 145.

Figure 3A:
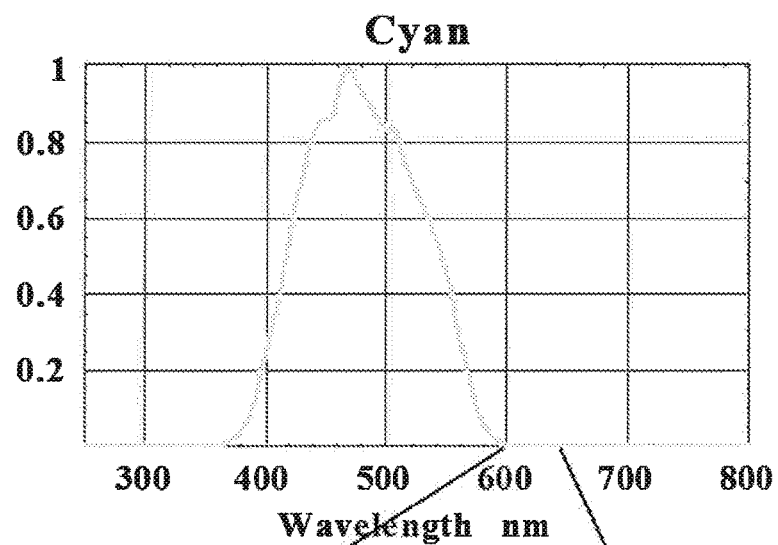
FIG. 3A illustrates an embodiment of a plot of transmission vs. wavelength for a cyan dye panel of the film.
Figure 3D:
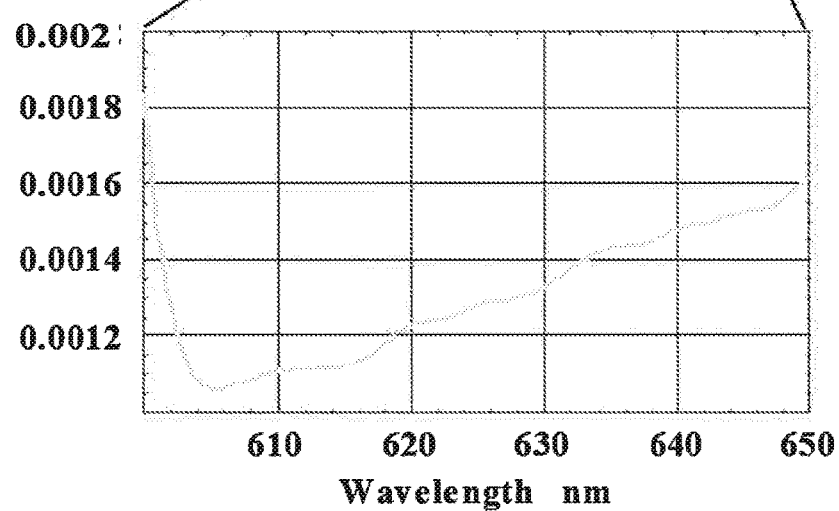
FIG. 3D illustrates an embodiment of a minimum transmission (maximum absorption) region of the cyan dye panel of the film.
Figures 3B, 3E:
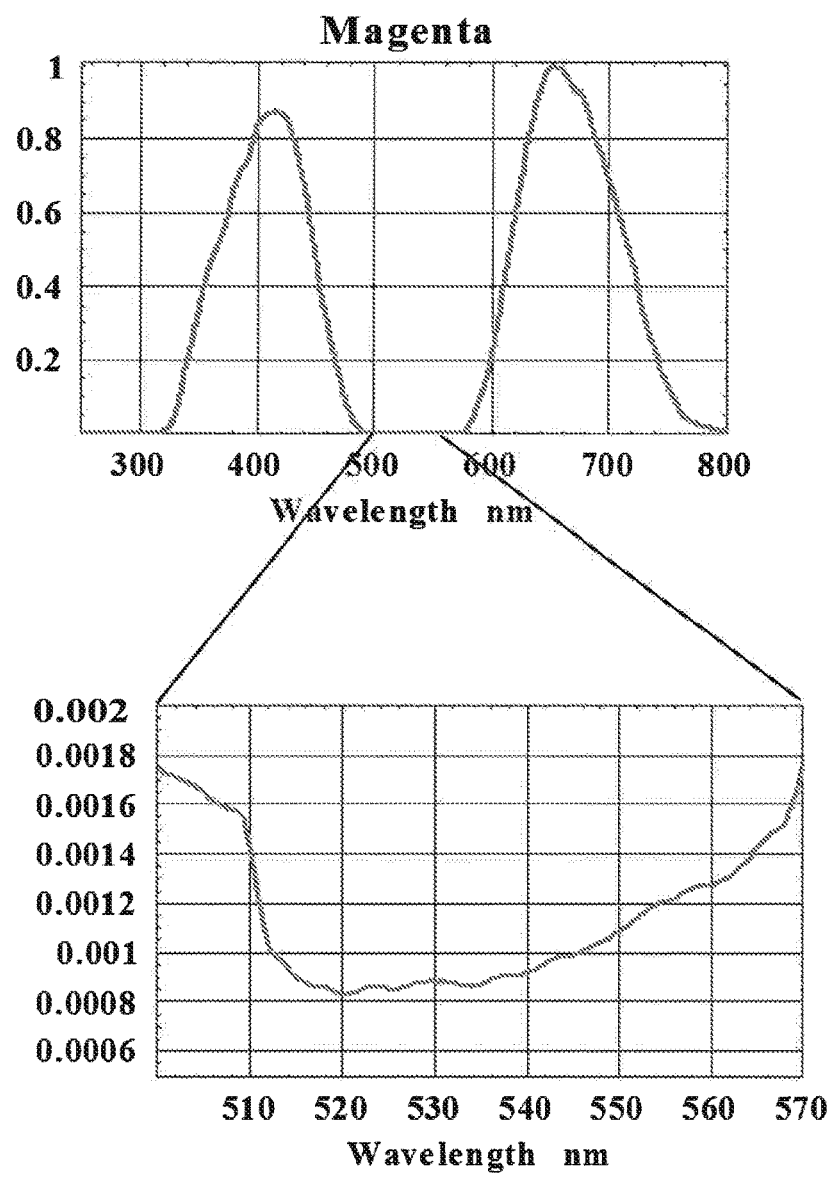
FIG. 3B illustrates an embodiment of a plot of transmission vs. wavelength for a magenta dye panel of the film.
FIG. 3E illustrates an embodiment of a minimum transmission (maximum absorption) region of the magenta dye panel of the film.
Figure 3C:
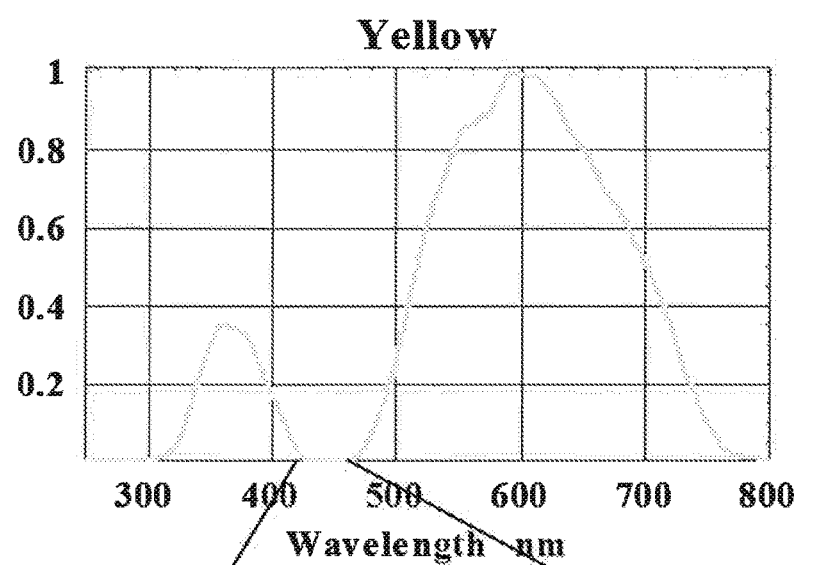
FIG. 3C illustrates an embodiment of a plot of transmission vs. wavelength for a yellow dye panel of the film.
Figure 3F:
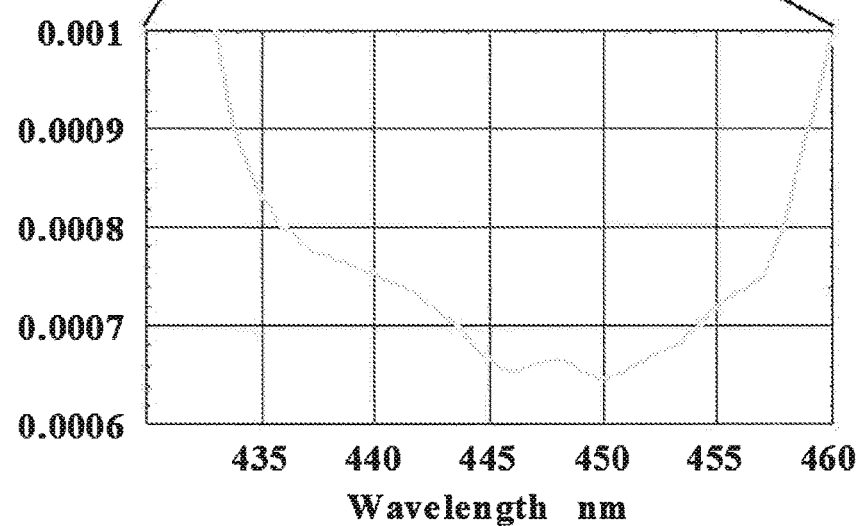
FIG. 3F illustrates an embodiment of a minimum transmission (maximum absorption) region of the yellow dye panel of the film.

FIGS. 3A-F provide a top row that shows plots of transmission vs. wavelength for cyan (FIG. 3A), magenta (FIG. 3B) and yellow (FIG. 3C) dye panels, and a bottom row that shows the minimum transmission (maximum absorption) region in the top row plots expanded in FIGS. 3D-F. Thermal dye printer film may be seen to have broadband transmission functions for cyan, magenta, and yellow. Selecting an illumination color near the minimum transmission (maximum absorption) has been found to provide good imaging results (best contrast, λc, Δλ). As illustrated, for cyan, the most attenuated wavelength is approximately 605 nm, for magenta it is approximately 520 nm, and for yellow it is approximately 450 nm. "Approximately" includes plus or minus 5 nm. Moreover, the illuminating wavelength can be adjusted to provide wavelength dependent image contrast. Image contrast can be matched to the dynamic range (contrast) of the camera.

Disclosed imaging systems may be embodied as manual systems or automatic systems. Regarding automatic imaging systems, the unused border around each image may be utilized. This border may be the same color as the frame (CYMK color panel) and may provide significant area to check the color of each frame. At the beginning of a frame, each light source may be pulsed and the camera may "see" which one has the highest and lowest transmission. In this way the frame color may be defined and the appropriate light color may be chosen to provide for a complete scan. Sources for the CYMK film used in a respective printer may produce a standard product, so that the colors are almost exactly the same from roll to roll of film for that printer. Moreover, all film manufacturers are generally expected to make the same color in their film.

The light sources may be narrow band light sources not adjustable (fixed) in wavelength to simplify the setup. Contrast adjustment, if desired, may be made in software and selectable by the user once an automatic first pass is completed. Contrast may be easily calculated for each frame and all frames may be adjusted by an on-board controller to be essentially equal. The user may change the contrast setting at any time.

Figure 4:
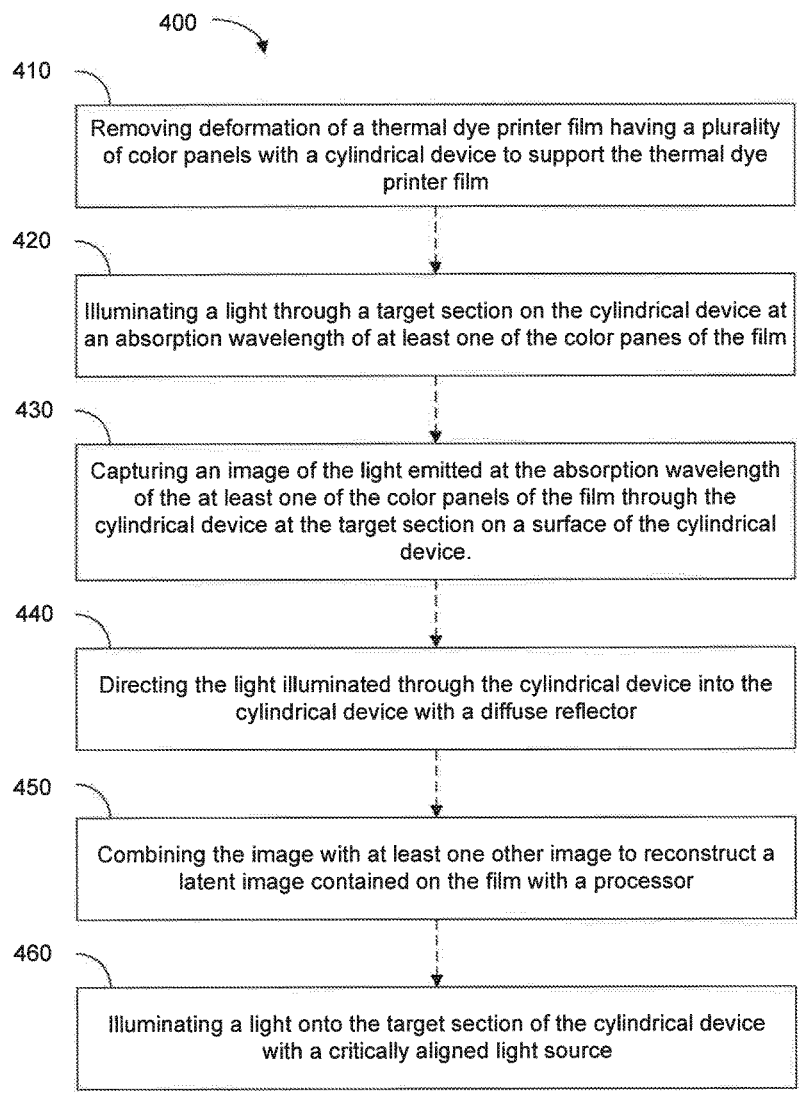
FIG. 4 illustrates a flowchart of an embodiment of a method.

FIG. 4 illustrates a flowchart of an embodiment of a method. The method 400 comprises removing deformation of a thermal dye printer film having a plurality of color panels with a cylindrical device configured to support the thermal dye printer film, at 410. The method 400 further comprises illuminating a light through a target section on the roller at an absorption wavelength of at least one of the color panels of the film, at 420. The method 400 also comprises capturing an image of the light emitted at the absorption wavelength of the at least one of the color panels of the film through the cylindrical device at the target section on a surface of the cylindrical device, at 430.

The method may further comprise directing the light illuminated through the cylindrical device into the cylindrical device with a diffuse reflector, at 440. The method 400 may further comprise combining the image with at least one other image to reconstruct a latent image contained on the film with a processor, at 450. The method 400 may further comprise illuminating a light onto the target section of the cylindrical device with a critically aligned light source, at 460. Though the method 400 is illustrated in a particular order, this order is not limiting as the steps shown may be placed in any order.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Therefore, the breadth and scope of the subject matter provided herein should not be limited by any of the above explicitly described embodiments. Rather, the scope of the embodiments should be defined in accordance with the following claims and their equivalents.

I claim:
1. A system comprising:
  a cylindrical device, having at least one transparent path therethrough, configured to support a thermal dye printer film, the film comprising at least one color panel;
  a light source configured to illuminate through the cylindrical device at an absorption wavelength of the at least one color panel of the film; and
  an imaging device configured to capture an image of the film with light emitted at the absorption wavelength of the at least one color panel of the film at a target location on the cylindrical device.

2. The system according to claim 1, further comprising a diffuse reflector configured to direct light illuminated from the light source through the cylindrical device.

3. The system according to claim 1, wherein the light source is configured to illuminate at each absorption wavelength of each color panel when the at least one color panel comprises a plurality of color panels.

4. The system according to claim 1, wherein the cylindrical device is a transparent cylindrical device.

5. The system according to claim 1, wherein the at least one transparent path of the cylindrical device is configured to direct illumination from the light source to a location where the imaging device captures the image.

6. The system according to claim 1, further comprising a processor configured to combine image data to reconstruct a latent image contained on the film.

7. The system according to claim 1, wherein the target location on the cylindrical device is configured to provide for the imaging device to capture line-by-line images of the film.

8. The system according to claim 1, further comprising a critically aligned light source configured to illuminate light onto the target location of the cylindrical device.

9. The system according to claim 8, wherein the critically aligned light source provides for specular reflection from the film.

10. A system for capturing a latent image from a thermal dye printer film having a plurality of color panels, the system comprising:
- an arcuate surface configured to provide for removal of a deformation in a thermal dye printer film and with a transparent path through the arcuate surface;
- a light source configured to illuminate through the arcuate surface at an absorption wavelength of at least one of the color panels of the film; and
- an imaging device configured to capture an image of the film with light emitted at the absorption wavelength of the at least one color panel of the film at a target location on the arcuate surface.

11. The system according to claim 10, further comprising a diffuse reflector configured to direct light illuminated from the light source through the arcuate surface.

12. The system according to claim 10, wherein the light source is configured to illuminate at each absorption wavelength of each color panel of the plurality of color panels.

13. The system according to claim 10, wherein the arcuate surface is a part of a transparent cylindrical device.

14. The system according to claim 10, wherein a section of the arcuate surface through which the light source illuminates to where the imaging device captures the image is transparent.

15. The system according to claim 10, further comprising a processor configured to combine image data to reconstruct a latent image contained on the film.

16. The system according to claim 10, wherein the target location on the arcuate surface is configured to provide for the imaging device to capture line-by-line images of the film.

17. The system according to claim 10, further comprising a critically aligned light source configured to illuminate light onto the target of the arcuate surface to provide for imaging a latent fingerprint located on the film.

18. The system according to claim 17, wherein the critically aligned light source provides for specular reflection from the film.

19. A method comprising:
- removing deformation of a thermal dye printer film having a plurality of color panels with a cylindrical device configured to support the thermal dye printer film;
- illuminating a light through a target section on the roller at an absorption wavelength of at least one of the color panels of the film; and
- capturing an image of the light emitted at the absorption wavelength of the at least one of the color panels of the film through the cylindrical device at the target section on a surface of the cylindrical device.

20. The method according to claim 19, further comprising directing the light illuminated through the cylindrical device into the cylindrical device with a diffuse reflector.

21. The method according to claim 19, further comprising combining the image with at least one other image to reconstruct a latent image contained on the film with a processor.

22. The method according to claim 19, further comprising illuminating a light onto the target section of the cylindrical device with a critically aligned light source.

\* \* \* \* \*